(12) United States Patent
Etzkorn et al.

(10) Patent No.: US 9,662,054 B2
(45) Date of Patent: *May 30, 2017

(54) SYMMETRICALLY ARRANGED SENSOR ELECTRODES IN AN OPHTHALMIC ELECTROCHEMICAL SENSOR

(71) Applicant: VERILY LIFE SCIENCES LLC, Mountain View, CA (US)

(72) Inventors: James Etzkorn, Mountain View, CA (US); Zenghe Liu, Alameda, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,202

(22) Filed: Jun. 17, 2015

(65) Prior Publication Data

US 2015/0282743 A1    Oct. 8, 2015

Related U.S. Application Data

(63) Continuation of application No. 13/919,764, filed on Jun. 17, 2013, now Pat. No. 9,084,561.

(51) Int. Cl.
*A61B 5/1486* (2006.01)
*A61B 5/1477* (2006.01)
(Continued)

(52) U.S. Cl.
CPC ............ *A61B 5/1486* (2013.01); *A61B 3/101* (2013.01); *A61B 5/0002* (2013.01);
(Continued)

(58) Field of Classification Search
CPC ........... G01N 27/3271; G01N 27/4166; G01N 27/30; G01N 27/26; G01N 33/50;
(Continued)

(56) References Cited

U.S. PATENT DOCUMENTS 3,958,560 A    5/1976  March
4,014,321 A    3/1977  March
(Continued)

FOREIGN PATENT DOCUMENTS

EP    0 369 942    5/1990
EP    0 686 372    12/1995
(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
(Continued)

*Primary Examiner* — Navin Natnithithadha
*Assistant Examiner* — Eric Messersmith
(74) *Attorney, Agent, or Firm* — Blakely Sokoloff Taylor & Zafman LLP

(57) ABSTRACT

An eye-mountable device includes an electrochemical sensor embedded in a polymeric material configured for mounting to a surface of an eye. The electrochemical sensor includes a working electrode, a reference electrode, and a reagent that selectively reacts with an analyte to generate a sensor measurement related to a concentration of the analyte in a fluid to which the eye-mountable device is exposed. The working electrode can have a first side edge and a second side edge. The reference electrode can be situated such that at least a portion of the first and second side edges of the working electrode are adjacent respective sections of the reference electrode.

20 Claims, 10 Drawing Sheets

(51) Int. Cl.

| | |
|---|---|
| *G01N 27/327* | (2006.01) |
| *A61B 5/00* | (2006.01) |
| *A61B 5/145* | (2006.01) |
| *A61B 3/10* | (2006.01) |
| *G01N 27/30* | (2006.01) |
| *G01N 27/416* | (2006.01) |
| *G02C 7/04* | (2006.01) |

(52) U.S. Cl.
CPC .......... *A61B 5/0004* (2013.01); *A61B 5/1477* (2013.01); *A61B 5/14507* (2013.01); *A61B 5/14532* (2013.01); *A61B 5/14546* (2013.01); *A61B 5/6821* (2013.01); *A61B 5/7264* (2013.01); *G01N 27/30* (2013.01); *G01N 27/3271* (2013.01); *G01N 27/4166* (2013.01); *G02C 7/04* (2013.01); *A61B 5/002* (2013.01); *A61B 2560/0214* (2013.01)

(58) Field of Classification Search
CPC . A61B 5/0002; A61B 5/14546; A61B 5/1477; A61B 3/101; A61B 5/14507; A61B 5/14532; A61B 5/6821; A61B 5/0004; A61B 2560/0214; A61B 5/05; A61B 5/7264; A61B 5/1486; C12N 9/00
See application file for complete search history.

(56) References Cited

U.S. PATENT DOCUMENTS

| | | | |
|---|---|---|---|
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,655,880 A | 4/1987 | Liu |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 8,446,341 B2 | 5/2013 | Amirparviz et al. |
| 8,608,310 B2 | 12/2013 | Otis et al. |
| 8,880,139 B1 | 11/2014 | Etzkorn et al. |
| 2002/0049389 A1 | 4/2002 | Abreu |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0170055 A2 | 7/2007 | Wilsey |
| 2007/0188710 A1 | 8/2007 | Hetling et al. |
| 2008/0208335 A1 | 8/2008 | Blum et al. |
| 2008/0217173 A1 | 9/2008 | Varney et al. |

(56) References Cited

U.S. PATENT DOCUMENTS

| | | |
|---|---|---|
| 2008/0218696 A1 | 9/2008 | Mir |
| 2009/0015785 A1 | 1/2009 | Blum et al. |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder et al. |
| 2012/0109296 A1 | 5/2012 | Fan |
| 2012/0130213 A1 | 5/2012 | Kusaka |
| 2012/0177576 A1 | 7/2012 | Hu |
| 2012/0201755 A1 | 8/2012 | Rozakis et al. |
| 2012/0245444 A1 | 9/2012 | Otis et al. |
| 2012/0259188 A1 | 10/2012 | Besling |
| 2014/0371558 A1 | 12/2014 | Etzkorn et al. |

FOREIGN PATENT DOCUMENTS

| | | |
|---|---|---|
| EP | 1 061 874 | 12/2000 |
| EP | 1 818 008 | 8/2007 |
| EP | 1 947 501 | 7/2008 |
| EP | 1 617 757 | 8/2009 |
| EP | 2 457 122 | 5/2012 |
| EP | 2 508 935 | 10/2012 |
| EP | 2 600 702 | 6/2013 |
| JP | 2011005261 A | 1/2001 |
| JP | 2002-528212 | 9/2002 |
| JP | 2003-507717 | 2/2003 |
| JP | 51-75498 | 4/2013 |
| WO | WO 95/04609 | 2/1995 |
| WO | WO 01/16641 | 3/2001 |
| WO | WO 01/34312 | 5/2001 |
| WO | WO 03/065876 | 8/2003 |
| WO | WO 2004/060431 | 7/2004 |
| WO | WO 2004/064629 | 8/2004 |
| WO | WO 2006/015315 | 2/2006 |
| WO | WO 2009/094643 | 7/2009 |
| WO | WO 2010/105728 | 9/2010 |
| WO | WO 2010/133317 | 11/2010 |
| WO | WO 2011/011344 | 1/2011 |
| WO | WO 2011/034592 | 3/2011 |
| WO | WO 2011/035228 | 3/2011 |
| WO | WO 2011/035262 | 3/2011 |
| WO | WO 2011/083105 | 7/2011 |
| WO | WO 2011/163080 | 12/2011 |
| WO | WO 2012/035429 | 3/2012 |
| WO | WO 2012/037455 | 3/2012 |
| WO | WO 2012/051167 | 4/2012 |
| WO | WO 2012/051223 | 4/2012 |
| WO | WO 2012/052765 | 4/2012 |
| WO | WO 2014/113174 A1 | 7/2014 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as noninvasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008, pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng, 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007, pp. 755-758.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng, 2012, pp. 1-10, vol. 22.

Yao, H. et al., "A Dual Microscale Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, 12 pages, vol. 6, No. 4.

Bionic contact lens 'to project emails before eyes,' http://www.kurzweilai.net/forums/topic/bionic-contact-lens-to-project-emails-before-eyes, Last accessed Mar. 14, 2012, 2 pages.

Brahim, et al., "Polypyrrole-hydrogel composites for the construction of clinically important biosensors," 2002, Biosensors & Bioelectronics, pp. 53-59, vol. 17.

(56) References Cited

OTHER PUBLICATIONS

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.

"Contact Lenses: Look Into My Eyes," The Economist, Jun. 2, 2011, http://www.economist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012, 8 pages.

Liao, et al., "A 3-μW CMOS Glucose Sensor for Wireless Contact-Lens Tear Glucose Monitoring ," IEEE Journal of Solid-State Circuits, Jan. 2012, pp. 335-344, vol. 47, No. 1.

Liao, et al., "A 3-μW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.

Lingley, et al., "Multipurpose integrated active contact lenses," SPIE, 2009, 2 pages.

Liu, et al., "Miniature Amperometric Self-Powered Continuous Glucose Sensor with Linear Response," Analytical Chemistry, 2012, 7 pages.

Loncar, et al., "Design and Fabrication of Silicon Photonic Crystal Optical Waveguides," Journal of Lightwave Technology, Oct. 2000, pp. 1402-1411, vol. 18, No. 10.

Murdan, "Electro-responsive drug delivery from hydrogels," Journal of Controlled Release, 2003, pp. 1-17, vol. 92.

Pandey, et al., "A Fully Integrated RF-Powered Contact Lens With a Single Element Display," IEEE Transactions on Biomedical Circuits and Systems, Dec. 2010, pp. 454-461, vol. 4, No. 6.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Selner, et al., "Novel Contact Lens Electrode Array for Multi-electrode Electroretinography (meERG)," IEEE, 2011, 2 pages.

Singh, et al., "Novel Approaches in Formulation and Drug Delivery using Contact Lenses," Journal of Basic and Clinical Pharmacy, May 2011, pp. 87-101, vol. 2, Issue 2.

Thomas, et al., "Functional Contact Lenses for Remote Health Monitoring in Developing Countries," IEEE Global Humanitarian Technology Conference, 2011, pp. 212-217, IEEE Computer Society.

Tweedie, et al., "Contact creep compliance of viscoelastic materials via nanoindentation," J. Mater. Res., Jun. 2006, pp. 1576-1589, vol. 21, No. 2, Materials Research Society.

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

Zarbin, et al., "Nanotechnology in ophthalmology," Can J Ophthalmol, 2010, pp. 457-476, vol. 45, No. 5.

Iwasaki et al., "Electrochemical Measurements with Interdigitated Array Microelectrodes," Current Separations 14:1 (1995), pp. 2-8.

Cohen et al., "Large-area interdigitated array microelectrodes for electrochemical sensing," Sensors and Actuators B 62 (2000) pp. 23-29.

PCT/US2014/034839, PCT International Search Report and Written Opinion mailed Aug. 11, 2014, 17 pages.

U.S. Appl. No. 13/919,764, filed Jun. 17, 2013, U.S. Office Action mailed Dec. 19, 2013, 48 pages.

U.S. Appl. No. 13/919,764, filed Jun. 17, 2013, U.S. Final Office Action mailed Jul. 2, 2014, 18 pages.

U.S. Appl. No. 13/919,764, filed Jun. 17, 2013, U.S. Notice of Allowance mailed Mar. 13, 2015, 13 pages.

U.S. Appl. No. 14/034,323, filed Sep. 23, 2013, U.S. Office Action mailed Dec. 18, 2013, 15 pages.

U.S. Appl. No. 14/034,323, filed Sep. 23, 2013, U.S. Notice of Allowance mailed Jul. 16, 2014, 55 pages.

PCT/US2014/034839—International Preliminary Report on Patentability, mailed Dec. 30, 2015, 12 pages.

AU 2014281160—Patent Examination Report No. 1, mailed Jun. 10, 2016, 3 pages.

AU 2014281160—Notice of Acceptance, mailed Aug. 25, 2016, 2 pages.

EP 14813015.6—Extended European Search Report, mailed Dec. 22, 2016, 9 pages.

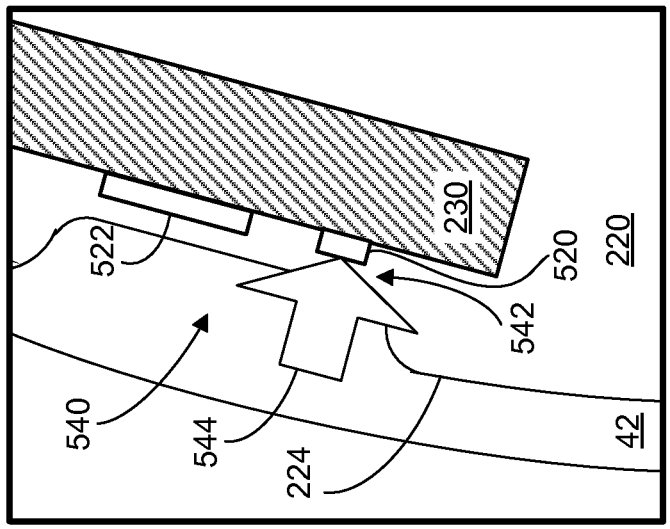
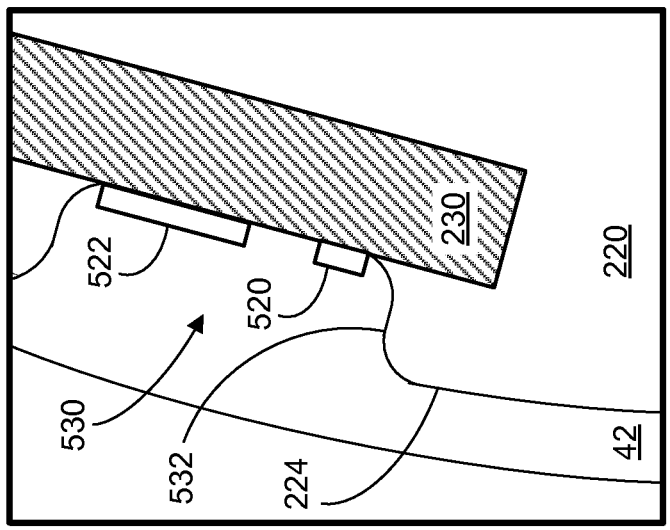
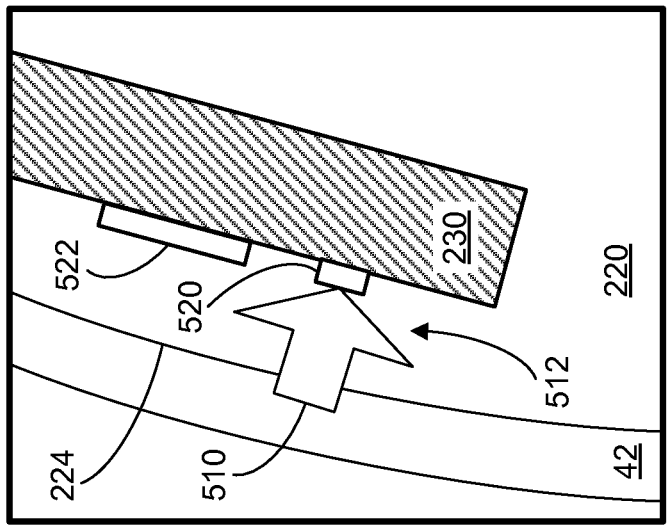

SYMMETRICALLY ARRANGED SENSOR ELECTRODES IN AN OPHTHALMIC ELECTROCHEMICAL SENSOR

CROSS-REFERENCE TO RELATED APPLICATION

The present patent application is a continuation of U.S. application Ser. No. 13/919,764 filed on Jun. 17, 2013.

BACKGROUND

Unless otherwise indicated herein, the materials described in this section are not prior art to the claims in this application and are not admitted to be prior art by inclusion in this section.

An electrochemical amperometric sensor measures a concentration of an analyte by measuring a current generated through electrochemical oxidation or reduction reactions of the analyte at a working electrode of the sensor. A reduction reaction occurs when electrons are transferred from the electrode to the analyte, whereas an oxidation reaction occurs when electrons are transferred from the analyte to the electrode. The direction of the electron transfer is dependent upon the electrical potentials applied to the working electrode by a potentiostat. A counter electrode and/or reference electrode is used to complete a circuit with the working electrode and allow the generated current to flow. When the working electrode is appropriately biased, the output current is proportional to the reaction rate, which provides a measure of the concentration of the analyte surrounding the working electrode.

In some examples, a reagent is localized proximate the working electrode to selectively react with a desired analyte. For example, glucose oxidase can be fixed near the working electrode to react with glucose and release hydrogen peroxide, which is then electrochemically detected by the working electrode to indicate the presence of glucose. Other enzymes and/or reagents can be used to detect other analytes.

SUMMARY

An ophthalmic device includes an electrochemical sensor configured to generate sensor readings based on analyte concentrations in solutions the ophthalmic device is exposed to. The electrochemical sensor includes a working electrode and a reference electrode arranged such that portions of the working electrode are at least partially surrounded on opposing sides by portions of the reference electrode. Upon applying a voltage across the sensor electrodes, the surrounded portions of the working electrode develop a voltage gradient that is substantially symmetric between the opposing sides. The two opposing sides are therefore at similar voltages and both side edges can induce electrochemical reactions with similar efficacy. Relative to an arrangement in which the working electrode has only one edge adjacent a reference electrode, the symmetric arrangement provides a relatively greater length of the edges of the working electrode facing the reference electrode.

Some embodiments of the present disclosure provide an eye-mountable device including a polymeric material, a substrate, an antenna, an electrochemical sensor, and a controller. The polymeric material can have a concave surface and a convex surface. The concave surface can be configured to be removably mounted over a corneal surface and the convex surface is configured to be compatible with eyelid motion when the concave surface is so mounted. The substrate can be at least partially embedded within the polymeric material. The antenna can be disposed on the substrate. The electrochemical sensor can be disposed on the substrate and can include a working electrode and a reference electrode. The working electrode can have a first side edge and a second side edge. The reference electrode can be situated such that at least a portion of the first and second side edges of the working electrode are adjacent respective sections of the reference electrode. The controller can be electrically connected to the electrochemical sensor and the antenna. The controller can be configured to: (i) apply a voltage between the working electrode and the reference electrode sufficient to generate an amperometric current related to the concentration of an analyte in a fluid to which the eye-mountable device is exposed; (ii) measure the amperometric current; and (iii) use the antenna to indicate the measured amperometric current.

Some embodiments of the present disclosure provide a system including an eye-mountable device and a reader. The eye-mountable device can include a polymeric material, a substrate, an antenna, an electrochemical sensor, and a controller. The polymeric material can have a concave surface and a convex surface. The concave surface can be configured to be removably mounted over a corneal surface and the convex surface is configured to be compatible with eyelid motion when the concave surface is so mounted. The substrate can be at least partially embedded within the polymeric material. The antenna can be disposed on the substrate. The electrochemical sensor can be disposed on the substrate and can include a working electrode and a reference electrode. The working electrode can have a first side edge and a second side edge. The reference electrode can be situated such that at least a portion of the first and second side edges of the working electrode are adjacent respective sections of the reference electrode. The controller can be electrically connected to the electrochemical sensor and the antenna. The controller can be configured to: (i) apply a voltage between the working electrode and the reference electrode sufficient to generate an amperometric current related to the concentration of an analyte in a fluid to which the eye-mountable device is exposed; (ii) measure the amperometric current; and (iii) use the antenna to indicate the measured amperometric current. The reader can include one or more antennas and a processing system. The one or more antennas can be configured to: (i) transmit radio frequency radiation to power the eye-mountable device, and (ii) receive indications of the measured amperometric current via backscatter radiation received at the one or more antennas. The processing system can be configured to determine a tear film analyte concentration value based on the backscatter radiation.

Some embodiments of the present disclosure include a device. The device can include a bio-compatible polymeric material, a substrate, an antenna, an electrochemical sensor, and a controller. The substrate can be at least partially embedded within the bio-compatible polymeric material. The antenna can be disposed on the substrate. The electrochemical sensor can be disposed on the substrate and can include a working electrode and a reference electrode. The working electrode can have a first side edge and a second side edge. The reference electrode can be situated such that at least a portion of the first and second side edges of the working electrode are adjacent respective sections of the reference electrode. The controller can be electrically connected to the electrochemical sensor and the antenna. The controller can be configured to: (i) apply a voltage between the working electrode and the reference electrode sufficient to generate an amperometric current related to the concentration of an analyte in a fluid to which the eye-mountable device is exposed; (ii) measure the amperometric current; and (iii) use the antenna to indicate the measured amperometric current.

Some embodiments of the present disclosure provide an eye-mountable device including a polymeric material. The eye-mountable device can include an electrochemical sensor with means for generating an amperometric current from sensor electrodes exposed to a solution including an analyte. The sensor electrodes can include means for providing an approximately symmetric voltage gradient to more than one side of a working electrode.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 5A shows an example configuration in which an electrochemical sensor detects an analyte that diffuses from a tear film through a polymeric material.

FIG. 5B shows an example configuration in which an electrochemical sensor detects an analyte in a tear film that contacts the sensor via a channel in a polymeric material.

FIG. 5C shows an example configuration in which an electrochemical sensor detects an analyte that diffuses from a tear film through a thinned region of a polymeric material.

DETAILED DESCRIPTION

Figure 1:
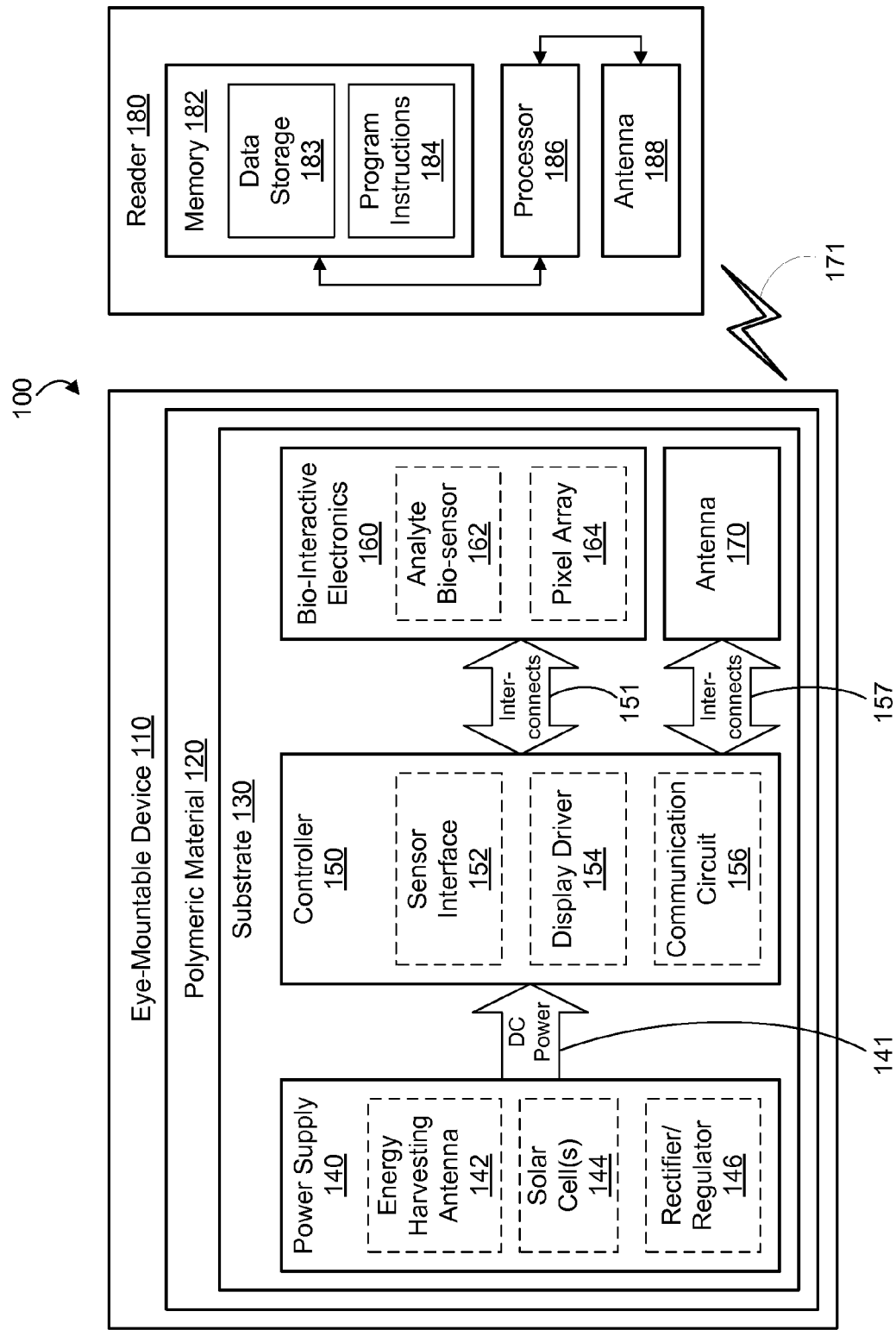
FIG. 1 is a block diagram of an example system that includes an eye-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

An ophthalmic sensing platform can include an electrochemical sensor, control electronics and an antenna all situated on a substrate embedded in a polymeric material formed to be contact mounted to an eye. The control electronics can operate the sensor to perform readings and can operate the antenna to wirelessly communicate the readings from the sensor to an external reader via the antenna. The polymeric material can be in the form of a round lens with a concave curvature configured to mount to a corneal surface of an eye. The substrate can be embedded near the periphery of the polymeric material to avoid interference with incident light received closer to the central region of the cornea. The sensor can be arranged on the substrate to face outward away from the corneal surface. A channel in the polymeric material can expose the sensor electrodes to tear film that coats the outer surface of the polymeric material, such as tear film distributed by eyelid motion.

The ophthalmic sensing platform can be powered via radiated energy harvested at the sensing platform. Power can be provided by light energizing photovoltaic cells included on the sensing platform. Additionally or alternatively, power can be provided by radio frequency energy harvested from the antenna. A rectifier and/or regulator can be incorporated with the control electronics to generate a stable DC voltage to power the sensing platform from the harvested energy. The antenna can be arranged as a loop of conductive material with leads connected to the control electronics. In some embodiments, such a loop antenna can wirelessly also communicate the sensor readings to an external reader by modifying the impedance of the loop antenna so as to modify backscatter radiation from the antenna.

Human tear fluid contains a variety of inorganic electrolytes (e.g., $Ca^{2+}$, $Mg^{2+}$, $Cl^-$), organic solutes (e.g., glucose, lactate, etc.), proteins, and lipids. A contact lens with one or more sensors that can measure one or more of these components provides a convenient non-invasive platform to diagnose or monitor health related problems. An example is a glucose sensing contact lens that can potentially be used for diabetic patients to monitor and control their blood glucose level.

A controller, which may include a potentiostat, is connected to the electrodes to bias the working electrode with respect to the reference electrode while monitoring the current between the two. The working electrode is biased to a suitable potential to generate electrochemical reactions of a particular analyte. The monitored current then provides an indication of analyte concentration.

In an electrochemical sensor with two electrodes, current-generating electrochemical reactions tend to occur with greatest efficiency along the working electrode at points nearest the reference electrode (e.g., where the local voltage gradient is greatest between the two electrodes). In some embodiments disclosed herein, a working electrode includes a section that is surrounded, on opposing side edges, by corresponding sections of the reference electrode. The increased length of the edges of the working electrode facing the reference electrode (e.g., two side edges versus one) can thereby increase the reaction area for electrochemical reactions, because reactions occur symmetrically along both opposing side edges of the portions of the working electrode surrounded by the reference electrode. Sensors incorporating such symmetric electrode arrangements can generate relatively greater amperometric currents for a given analyte concentration, thereby enhancing the sensitivity of such sensors. Moreover, symmetric electrode arrangements disclosed herein can effectively increase the reaction area of the sensor electrodes (e.g., the region immediately adjacent the side edges of the working electrode that are adjacent the reference electrode) without substantially increasing the total electrode size.

The amperometric current generated by a particular sensor depends, among other things, on the size of the electrochemical reaction region on the working electrode where reduction or oxidation reactions occur. Such current-generating reactions occur at the working electrode preferentially along the edges of the working electrode nearest the reference electrode (i.e., where the voltage gradient is greatest). Thus, the size of the reaction region of a given electrochemical sensor is determined, at least in part, by the length of the working electrode side edges that are adjacent to portions of the reference electrode.

In some examples, the two electrodes can be arranged such that the working electrode is surrounded on both sides by portions of the reference electrode. As such, current-generating electrochemical reactions can occur at both side edges of the working electrode with comparable efficacy. For example, in an approximately co-planar electrode arrangement, the working electrode may include narrow extensions that are positioned between portions of the reference electrode on either side. In some cases the two electrodes may each resemble a comb, with a pattern of fingers extending from a base (e.g., the working electrode can have fingers about 25 µm wide and the reference electrode can have fingers about 125 µm wide). The two sets of fingers from the respective electrodes can then be positioned to interlock, without contacting, such that a given one of the working electrode extensions/fingers is surrounded by respective portions of the reference electrode. The resulting alternating (or interdigitated) geometry can desirably generate a relatively greater sensor current for a given analyte concentration due to the increased reaction region that includes both side edges of the working electrode.

Some embodiments of the present disclosure therefore provide for electrode arrangements in which a working electrode includes at least one extension surrounded on both sides by portions of a reference electrode. The working electrode extension (and corresponding portions of the reference electrode) can be arranged as interdigitated substantially parallel bars or as concentric rings, for example. In either case, the working electrode can includes a narrow extension that is surrounded by relatively wider portions of the reference electrode on both sides. As a result, during operation of such an electrochemical sensor, the working electrode causes current-generating reactions to take place along both side edges of the two narrow extension(s) with substantially comparable efficacy. The resulting amperometric current is therefore greater than would be produced by a sensor with a working electrode only adjacent a reference electrode along a single side edge.

II. Example Ophthalmic Electronics Platform

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc. to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of resists, masks, and deposition techniques can be employed to pattern materials on the substrate 130. The substrate 130 can be a relatively rigid material, such as polyethylene terephthalate ("PET") or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in the center region of the eye-mountable device 110. The bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be perceived by the eye according to display instructions. Thus, the bio-interactive electronics 160 can optionally be positioned in the center of the eye-mountable device so as to generate perceivable visual cues to a wearer of the eye-mountable device 110, such as by displaying information via the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected to the output of the rectifier 146 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such as analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of glucose oxidase ("GOx") proximal to the working electrode can catalyze glucose oxidation to generate hydrogen peroxide ($H_2O_2$). The hydrogen peroxide can then be electrooxidized at the working electrode, which releases electrons to the working electrode, resulting in an amperometric current that can be measured through the working electrode.

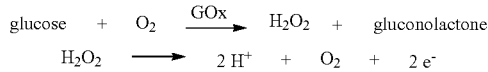

$$H_2O_2 \longrightarrow 2H^+ + O_2 + 2e^-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportional to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, micro-electromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivably by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earing, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 180 (e.g., via the communication circuit 156). The sensor reading can be communicated by, for example, modulating an impedance of the communication antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Figure 2A:
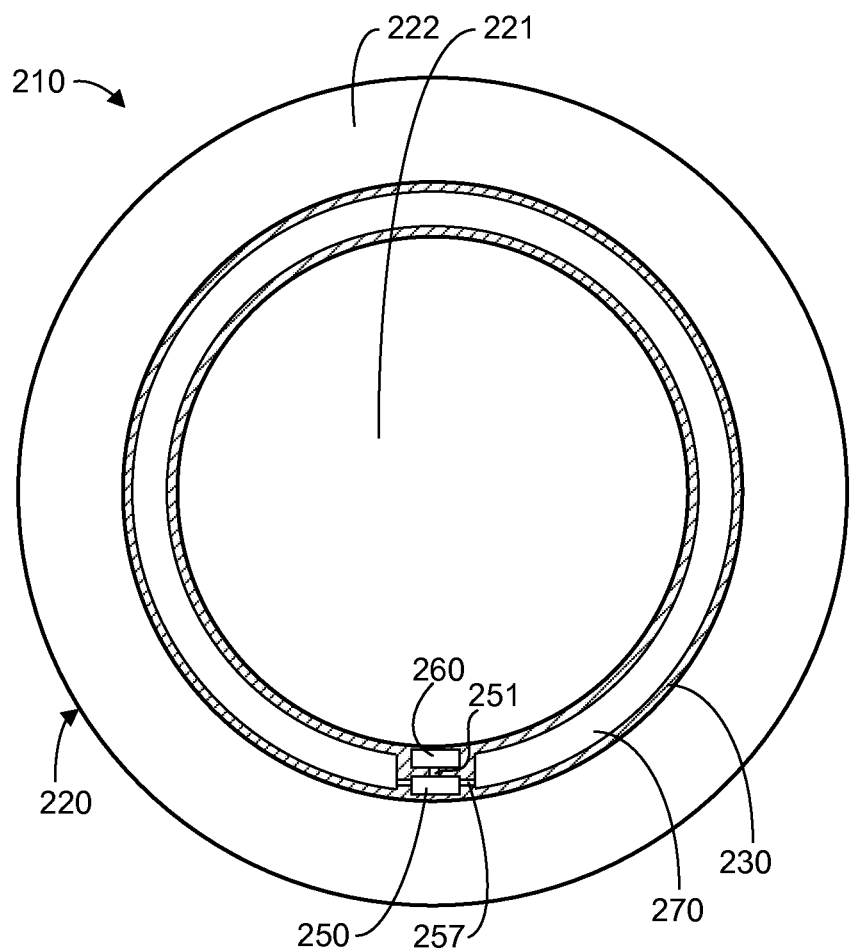
FIG. 2A is a top view of an example eye-mountable device.
Figure 2B:
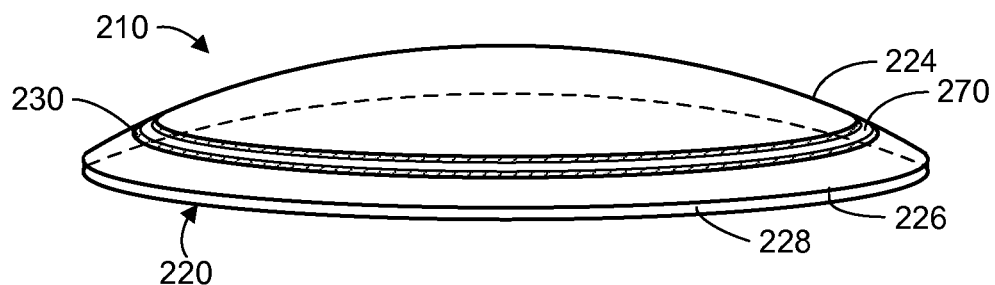
FIG. 2B is an aspect view of the example eye-mountable device shown in FIG. 2A.

FIG. 2A is a top view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved to extend out of the page, whereas the central region 221, near the center of the disk is curved to extend into the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a flat, circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and sensor electronics 260 are disposed on the embedded substrate 230. The controller 250 can be a chip including logic elements configured to operate the sensor electronics 260 and the loop antenna 270. The controller 250 is electrically connected to the loop antenna 270 by interconnects 257 also situated on the substrate 230. Similarly, the controller 250 is electrically connected to the sensor electronics 260 by an interconnect 251. The interconnects 251, 257, the loop antenna 270, and any conductive electrodes (e.g., for an electrochemical analyte sensor, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the convex surface 224 of the eye-mountable device 210, the bio-interactive electronics module 260 is mounted to a side of the substrate 230 facing the convex surface 224. Where the bio-interactive electronics module 260 includes an analyte bio-sensor, for example, mounting such a bio-sensor on the substrate 230 to be close to the convex surface 224 allows the bio-sensor to sense analyte concentrations in tear film 42 coating the convex surface 224 of the polymeric material 220 (e.g., a tear film layer distributed by eyelid motion). However, the electronics, electrodes, etc. situated on the substrate 230 can be mounted to either the "inward" facing side (e.g., situated closest to the concave surface 226) or the "outward" facing side (e.g., situated closest to the convex surface 224). Moreover, in some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some examples, to allow additional flexibility along the curvature of the polymeric material, the loop antenna 270 can include multiple substantially concentric sections electrically joined together. Each section can then flex independently along the concave/convex curvature of the eye-mountable device 210. In some examples, the loop antenna 270 can be formed without making a complete loop. For instances, the antenna 270 can have a cutout to allow room for the controller 250 and sensor electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and sensor electronics 260. Interconnects between the ends of such a wound antenna (e.g., the antenna leads) can then be passed through the substrate 230 to the controller 250.

Figure 2D:
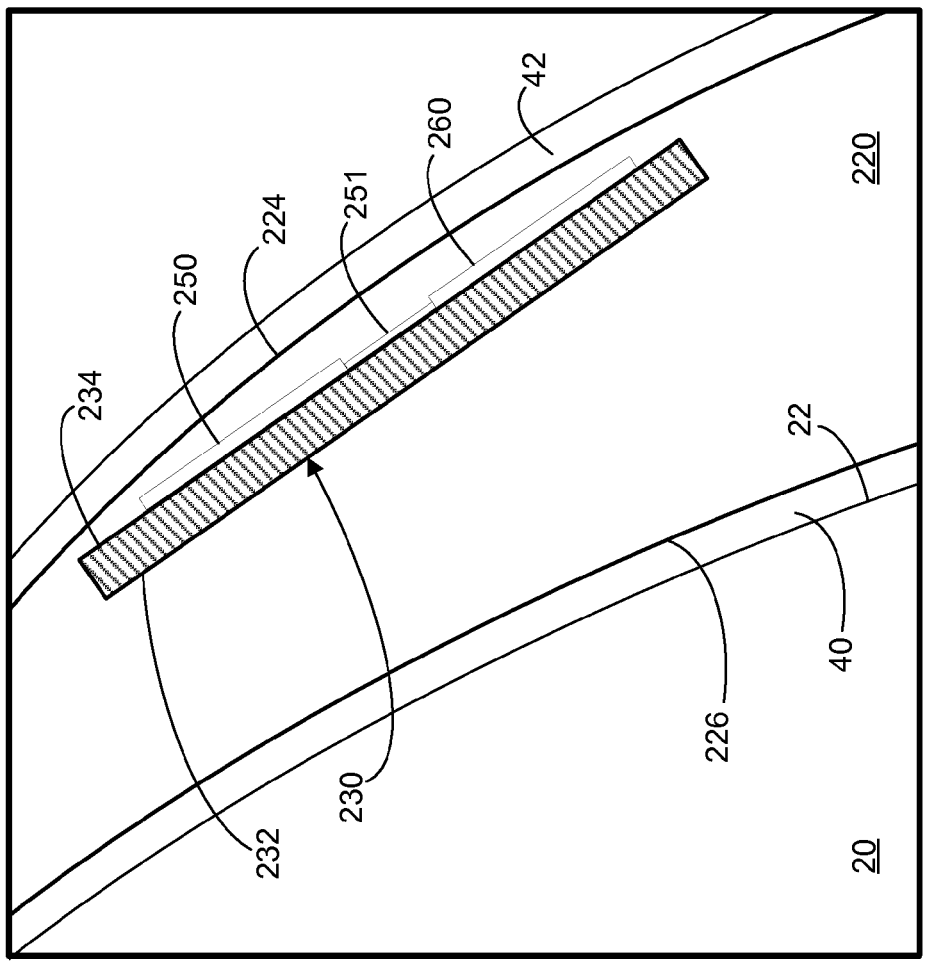
FIG. 2D is a side cross-section view enhanced to show the tear film layers surrounding the surfaces of the example eye-mountable device when mounted as shown in FIG. 2C.
Figure 2C:
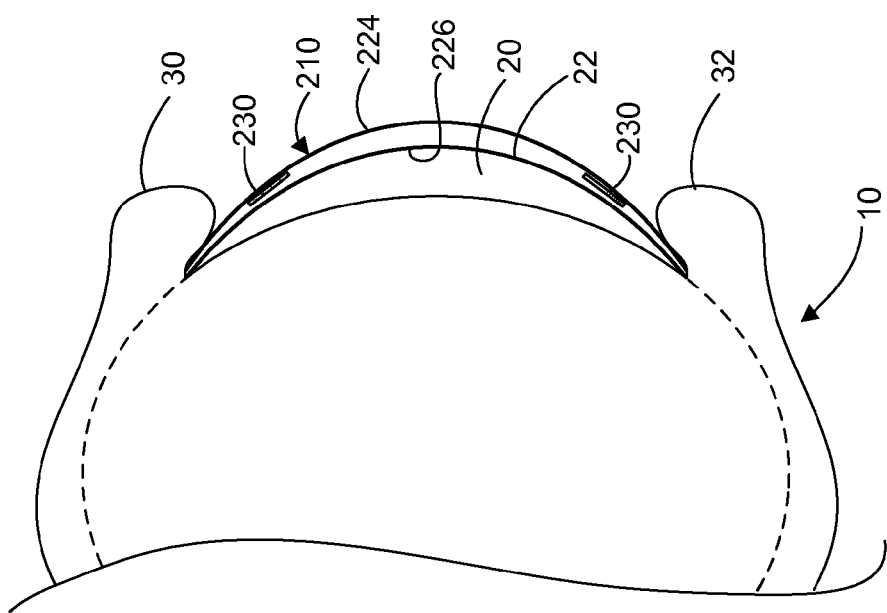
FIG. 2C is a side cross-section view of the example eye-mountable device shown in FIGS. 2A and 2B while mounted to a corneal surface of an eye.

FIG. 2C is a side cross-section view of the example eye-mountable electronic device 210 while mounted to a corneal surface 22 of an eye 10. FIG. 2D is a close-in side cross-section view enhanced to show the sensor electronics 260 on the example eye-mountable device 210 when mounted as shown in FIG. 2C. As shown in FIG. 2D, while mounted to the corneal surface 22, tear film layers 40, 42 coat the concave surface 226 and convex surface 224. It is noted that the relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the convex surface 224. As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the sensor electronics 260, controller 250, and conductive interconnect 251 are mounted on the outward-facing surface 234 such that the sensor electronics 260 are relatively closer in proximity to the convex surface 224 than if they were mounted on the inward-facing surface 232.

III. An Ophthalmic Electrochemical Analyte Sensor

Figure 3:
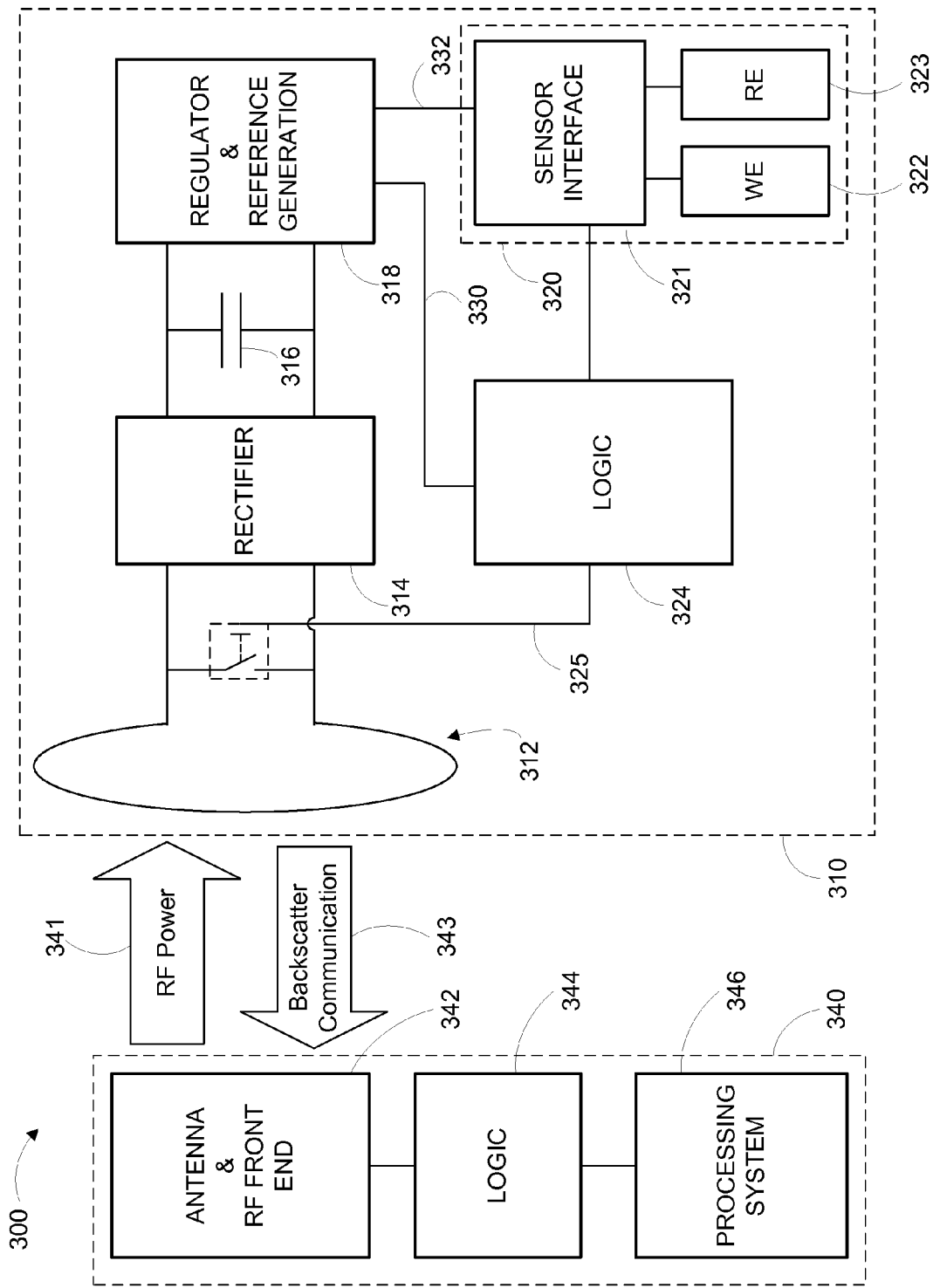
FIG. 3 is a functional block diagram of an example system for electrochemically measuring a tear film analyte concentration.

FIG. 3 is a functional block diagram of a system 300 for electrochemically measuring a tear film analyte concentration. The system 300 includes an eye-mountable device 310 with embedded electronic components powered by an external reader 340. The eye-mountable device 310 includes an antenna 312 for capturing radio frequency radiation 341 from the external reader 340. The eye-mountable device 310 includes a rectifier 314, an energy storage 316, and regulator 318 for generating power supply voltages 330, 332 to operate the embedded electronics. The eye-mountable device 310 includes an electrochemical sensor 320 with a working electrode 322 and a reference electrode 323 driven by a sensor interface 321. The eye-mountable device 310 includes hardware logic 324 for communicating results from the sensor 320 to the external reader 340 by modulating (325) the impedance of the antenna 312. Similar to the eye-mountable devices 110, 210 discussed above in connection with FIGS. 1 and 2, the eye-mountable device 310 can include a mounting substrate embedded within a polymeric material configured to be mounted to an eye. The electrochemical sensor 320 can be situated on a mounting surface of such a substrate proximate the surface of the eye (e.g., corresponding to the bio-interactive electronics 260 on the inward-facing side 232 of the substrate 230) to measure analyte concentration in a tear film layer interposed between the eye-mountable device 310 and the eye (e.g., the inner tear film layer 40 between the eye-mountable device 210 and the corneal surface 22).

With reference to FIG. 3, the electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidation voltage between the working electrode 322 and the reference electrode 323 to oxidize the products from the reagent-catalyzed analyte at the working electrode 322. The sensor interface 321 measures the amperometric current and provides an output to the hardware logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter high frequency noise on the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324. While powered, the sensor 320 and hardware logic 324 are configured to generate and measure an amperometric current and communicate the results.

The sensor results can be communicated back to the external reader 340 via backscatter radiation 343 from the antenna 312. The hardware logic 324 receives the output current from the electrochemical sensor 320 and modulates (325) the impedance of the antenna 312 in accordance with the amperometric current measured by the sensor 320. The antenna impedance and/or change in antenna impedance is detected by the external reader 340 via the backscatter signal 343. The external reader 340 can include an antenna front end 342 and logic components 344 to decode the information indicated by the backscatter signal 343 and provide digital inputs to a processing system 346. The external reader 340 associates the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or a network-connected memory.

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

Figure 4A:
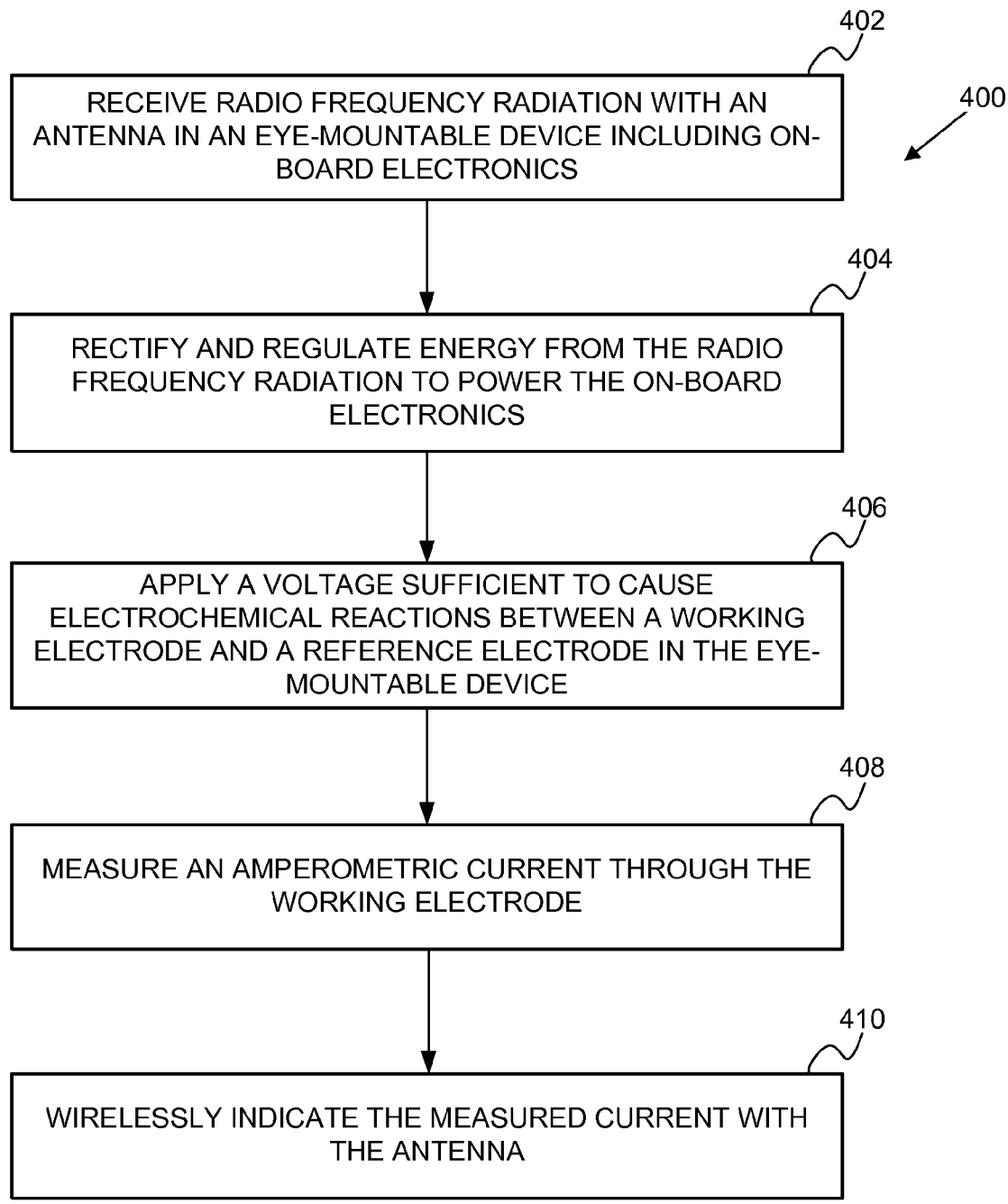
FIG. 4A is a flowchart of an example process for operating an electrochemical sensor in an eye-mountable device to measure a tear film analyte concentration.

FIG. 4A is a flowchart of a process 400 for operating an amperometric sensor in an eye-mountable device to measure a tear film analyte concentration. Radio frequency radiation is received at an antenna in an eye-mountable device including an embedded electrochemical sensor (402). Electrical signals due to the received radiation are rectified and regulated to power the electrochemical sensor and associated controller (404). For example, a rectifier and/or regulator can be connected to the antenna leads to output a DC supply voltage for powering the electrochemical sensor and/or controller. A voltage sufficient to cause electrochemical reactions at the working electrode is applied between a working electrode and a reference electrode on the electrochemical sensor (406). An amperometric current is measured through the working electrode (408). For example, a potentiostat can apply a voltage between the working and reference electrodes while measuring the resulting amperometric current through the working electrode. The measured amperometric current is wirelessly indicated with the antenna (410). For example, backscatter radiation can be manipulated to indicate the sensor result by modulating the antenna impedance.

Figure 4B:
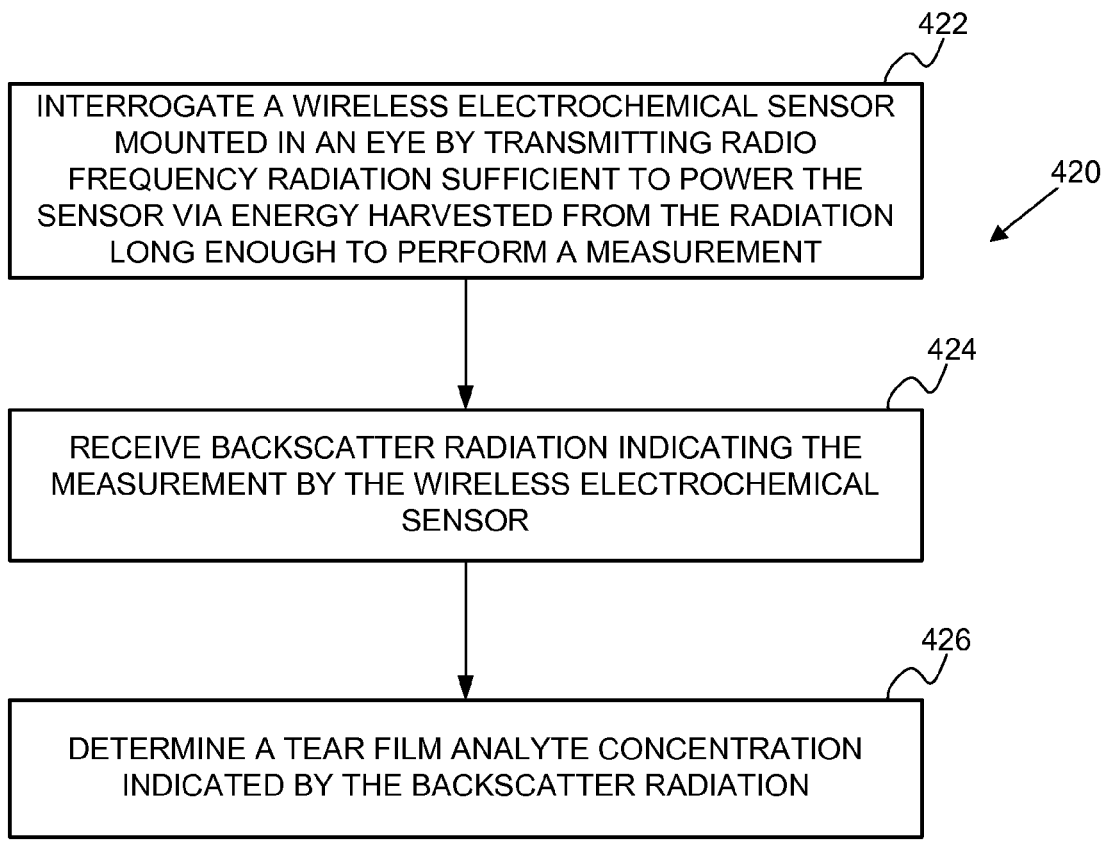
FIG. 4B is a flowchart of an example process for operating an external reader to interrogate an electrochemical sensor in an eye-mountable device to measure a tear film analyte concentration.

FIG. 4B is a flowchart of a process 420 for operating an external reader to interrogate an amperometric sensor in an eye-mountable device to measure a tear film analyte concentration. Radio frequency radiation is transmitted to an electrochemical sensor mounted in an eye from the external reader (422). The transmitted radiation is sufficient to power the electrochemical sensor with energy from the radiation for long enough to perform a measurement and communicate the results (422). For example, the radio frequency radiation used to power the electrochemical sensor can be similar to the radiation 341 transmitted from the external reader 340 to the eye-mountable device 310 described in connection with FIG. 3 above. The external reader then receives backscatter radiation indicating the measurement by the electrochemical analyte sensor (424). For example, the backscatter radiation can be similar to the backscatter signals 343 sent from the eye-mountable device 310 to the external reader 340 described in connection with FIG. 3 above. The backscatter radiation received at the external reader is then associated with a tear film analyte concentration (426). In some cases, the analyte concentration values can be stored in the external reader memory (e.g., in the processing system 346) and/or a network-connected data storage.

For example, the sensor result (e.g., the measured amperometric current) can be encoded in the backscatter radiation by modulating the impedance of the backscattering antenna. The external reader can detect the antenna impedance and/or change in antenna impedance based on a frequency, amplitude, and/or phase shift in the backscatter radiation. The sensor result can then be extracted by associating the impedance value with the sensor result by reversing the encoding routine employed within the eye-mountable device. Thus, the reader can map a detected antenna impedance value to an amperometric current value. The amperometric current value is approximately proportionate to the tear film analyte concentration with a sensitivity (e.g., scaling factor) relating the amperometric current and the associated tear film analyte concentration. The sensitivity value can be determined in part according to empirically derived calibration factors, for example.

IV. Analyte Transmission to the Electrochemical Sensor

FIG. 5A shows an example configuration in which an electrochemical sensor detects an analyte from the outer tear film layer 42 coating the polymeric material 220. The electrochemical sensor can be similar to the electrochemical sensor 320 discussed in connection with FIG. 3 and includes a working electrode 520 and a reference electrode 522. The working electrode 520 and the reference electrode 522 are each mounted on an outward-facing side 224 of the substrate 230. The substrate 230 is embedded in the polymeric material 220 of the eye-mountable device 210 such that the electrodes 520, 522 of the electrochemical sensor are entirely covered by an overlapping portion 512 of the polymeric material 220. The electrodes 520, 522 in the electrochemical sensor are thus separated from the outer tear film layer 42 by the thickness of the overlapping portion 512. For example, the thickness of the overlapping region 512 can be approximately 10 micrometers.

An analyte in the tear film 42 diffuses through the overlapping portion 512 to the working electrode 520. The diffusion of the analyte from the outer tear film layer 42 to the working electrode 520 is illustrated by the directional arrow 510. The current measured through the working electrode 520 is based on the electrochemical reaction rate at the working electrode 520, which in turn is based on the amount of analyte diffusing to the working electrode 520. The amount of analyte diffusing to the working electrode 520 can in turn be influenced both by the concentration of analyte in the outer tear film layer 42, the permeability of the polymeric material 220 to the analyte, and the thickness of the overlapping region 512 (i.e., the thickness of polymeric material the analyte diffuses through to reach the working electrode 520 from the outer tear film layer 42). In the steady state approximation, the analyte is resupplied to the outer tear film layer 42 by surrounding regions of the tear film 42 at the same rate that the analyte is consumed at the working electrode 520. Because the rate at which the analyte is resupplied to the probed region of the outer tear film layer 42 is approximately proportionate to the tear film concentration of the analyte, the current (i.e., the electrochemical reaction rate) is an indication of the concentration of the analyte in the outer tear film layer 42.

FIG. 5B shows an example configuration in which an electrochemical sensor detects an analyte from the tear film that contacts the sensor via a channel 530 in the polymeric material 220. The channel 530 has side walls 532 that connect the convex surface 224 of the polymeric material 220 to the substrate 230 and/or electrodes 520, 522. The channel 530 can be formed by pressure molding or casting the polymeric material 220 for example. The channel 530 can also be formed by selectively removing the polymeric material covering the sensor electrodes 520, 522 following encapsulation. For example, an oxygen plasma treatment can be used to etch away the polymeric material covering the sensor electrodes so as to expose the sensor electrodes 520, 522. In some cases, the sensor electrodes 520, 522 can be formed of a material that is not readily etched by an oxygen plasma treatment, such as a metal material, for example. Thus, the sensor electrodes may function as an etch stop when forming the channel 530. The height of the channel 530 (e.g., the length of the sidewalls 532) corresponds to the separation between the inward-facing surface of the substrate 230 and the convex surface 224. That is, where the substrate 230 is positioned about 10 micrometers from the convex surface 224, the channel 530 is approximately 10 micrometers in height. The channel 530 fluidly connects the outer tear film layer 42 to the sensor electrodes 520, 522. Thus, the working electrode 520 is directly exposed to the outer tear film layer 42. As a result, analyte transmission to the working electrode 520 is unaffected by the permeability of the polymeric material 220 to the analyte of interest. The resulting indentation in the convex surface 224 also creates a localized increased volume of the tear film 42 near the sensor electrodes 520, 522. The volume of analyte tear film that contributes analytes to the electrochemical reaction at the working electrode 520 (e.g., by diffusion) is thereby increased. The sensor shown in FIG. 5B is therefore less susceptible to a diffusion-limited electrochemical reaction, because a relatively greater local volume of tear film surrounds the sampled region to contribute analytes to the electrochemical reaction.

FIG. 5C shows an example configuration in which the electrochemical sensor detects an analyte from the tear film 42 that diffuses through a thinned region 542 of the polymeric material 220. The thinned region 542 can be formed as an indentation 540 in the convex surface 224 (e.g., by molding, casting, etching, etc.). The thinned region 542 of the polymeric material 220 substantially encapsulates the electrodes 520, 522, so as to maintain a biocompatible coating between the sensor electrodes 520, 522 and anything in contact with the convex surface 224, such as the eyelids 30, 32, for example. The indentation 542 in the convex surface 224 also creates a localized increased volume of the tear film 42 near the sensor electrodes 520, 522. A directional arrow 544 illustrates the diffusion of the analyte from the outer tear film layer 42 to the working electrode 520.

While not specifically illustrated, the sensor electrodes 520, 522 may be positioned on the reverse side of the substrate 230, closer to the concave surface 226 of the polymeric material 220 and the inner tear film layer 40. Channels and/or thinned regions may be provided in the concave surface 226 to expose the sensor electrodes to the tear film and/or facilitate diffusion of the analyte to the sensor electrodes.

V. Example Symmetric Electrode Arrangements

In some examples, an electrochemical sensor is arranged such that portions of the working electrode are at least partially surrounded on opposing sides by portions of the reference electrode. As such, upon applying a voltage across the sensor electrodes, the surrounded portions of the working electrode develop a voltage gradient that is substantially symmetric between the opposing sides. The two opposing sides are therefore at similar voltages and both side edges can therefore induce electrochemical reactions with similar efficiency. Arranging the working electrode to be symmetrically surrounded by portions of the reference electrode can thereby increase the total length of the working electrode that is proximate the reference electrode (e.g., faces the reference electrode), relative to a sensor with a working electrode facing a reference electrode on one side, but not both sides. Electrochemical reactions tend to occur with greatest efficacy along the working electrode at points nearest the reference electrode (e.g., where the local voltage gradient is greatest between the two electrodes). The increased length of the working electrode facing the reference electrode (e.g., two side edges versus one) can thereby increase the reaction area for electrochemical reactions, because reactions occur symmetrically along both opposing side edges of the portions of the working electrode surrounded by the reference electrode. Sensors incorporating such symmetric electrode arrangements can generate relatively greater amperometric currents for a given analyte concentration, thereby enhancing the sensitivity of such sensors. Moreover, symmetric electrode arrangements disclosed herein can effectively increase the reaction area of the sensor electrodes without substantially increasing the total electrode size.

Figure 6A:
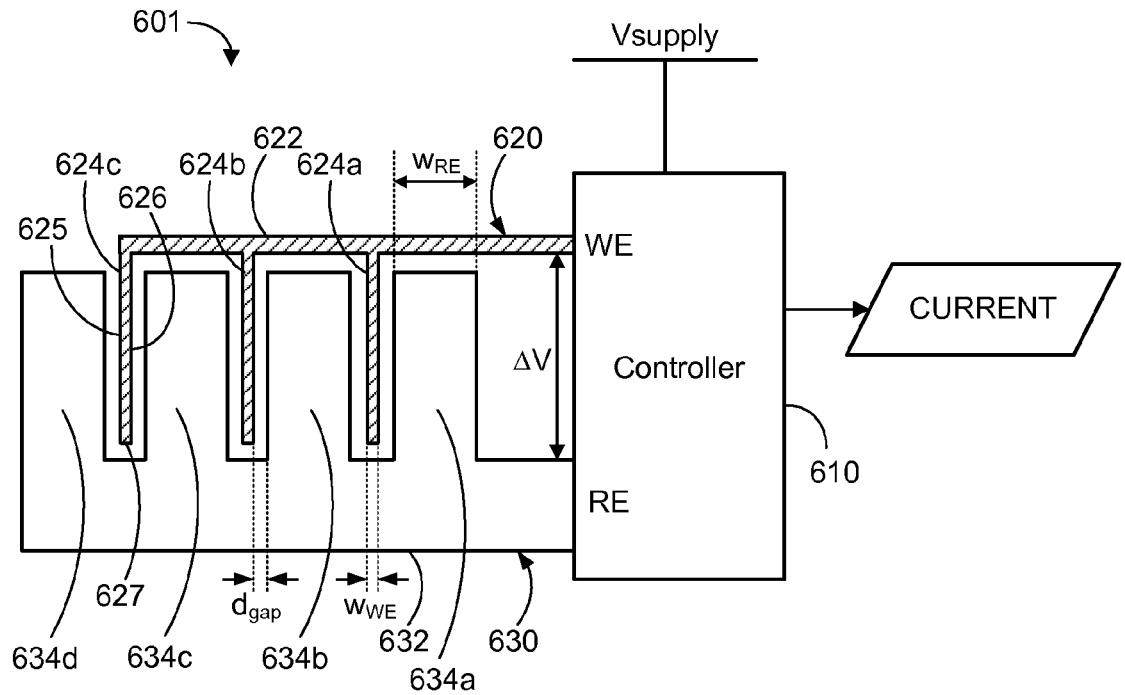
FIG. 6A illustrates one example symmetric arrangement for electrodes in an electrochemical sensor.

FIG. 6A illustrates one example symmetric arrangement for electrodes in an electrochemical sensor 601. The arrangement illustrated by FIG. 6A is not drawn to scale, but instead is provided for explanatory purposes to describe an example arrangement. The electrochemical sensor 601 can be included in an eye-mountable device for detecting a tear film concentration of an analyte (e.g., the eye-mountable devices described in connection with FIGS. 1-3 above). The electrochemical sensor includes a working electrode 620 and a reference electrode 630 arranged on a substrate.

The electrodes 620, 630 are each electrically connected to a controller 610 which operates the sensor 601 by applying a voltage difference $\Delta V$ between the working electrode 620 and the reference electrode 630. The voltage difference $\Delta V$ can be a reduction voltage sufficient to cause a reduction reaction at the working electrode 620 that releases electrons from the working electrode 620 and thereby generates an amperometric current that can be measured through the working electrode 620. Additionally or alternatively, the voltage difference $\Delta V$ can be an oxidization voltage sufficient to cause an oxidization reaction at the working electrode 620 that contributes electrons to the working electrode 620 and thereby generates an amperometric current that can be measured through the working electrode 620. The controller 610 is powered by a supply voltage Vsupply and outputs an indication of the amperometric current. In some embodiments, the controller 610 may include a potentiostat.

For purposes of clarity in the drawings only, the working electrode 620 is illustrated with a hatch pattern, while the reference electrode 630 is not. The working electrode 620 includes a base 622 and finger extensions 624a-c. Similarly, the reference electrode 630 includes a base 632 and multiple finger extensions 634a-d. The working electrode 620 and the reference electrode 630 can be arranged such that the finger extensions 624a-c and 634a-d of the two electrodes 620, 630 are interdigitated with one another. In some examples, the sensor electrodes 620, 630 can be at least approximately co-planar (e.g., disposed on a common substrate). In some examples, the extensions 624a-c, 634a-d can each extend at least approximately perpendicular to the respective bases 622, 632 of the sensor electrodes. In some examples, the extensions 624a-c, 634a-d can extend at least approximately in parallel with one another. In some examples, the extensions 624a-c of the working electrode 620 can be at least approximately equidistant from nearest ones of the reference electrode extensions 634a-d, along the side edges of each extension 624a-c.

In some examples, the extensions 624a-c of the working electrode 620 are at least partially surrounded on opposing sides by the extensions 634a-d of the reference electrode 630. For example, the extension 624c of the working electrode extends from the base 622 from a point near the base 622 to a distal end 627. The extension 624c includes a first side edge 625 and a second side edge 626 opposite the first side. The first and second side edges 625, 626 define the width of the extension 624c (e.g., similar to the width of the working electrode extension 624a labeled $w_{WE}$ in FIG. 6A). The first side edge 625 of the working electrode extension 624c is adjacent one extension 634d of the reference electrode, and the second side edge 626 is adjacent another extension 634c of the reference electrode. The inter-electrode spacing between the extension 624c and the two reference electrode extensions 634c-d (e.g., the gap between the first side edge 625 and the extension 634d and the gap between the second side edge 626 and the extension 634c) can be similar along both side edges 625, 626. For example, both sides can have an approximately uniform gap distance (e.g., the gap distance $d_{gap}$ labeled in FIG. 6A). In another example, both sides can have a tapered (or other varying) gap distance that varies symmetrically between the base 622 and the distal end 627. The gap distance dgap may be approximately equal to the working electrode width $w_{WE}$, or may be less than or greater than the working electrode $w_{WE}$. As a result of the symmetric arrangement, the voltage potential is similar along both side edges 625, 626 of the working electrode extension 624c while a voltage is applied across the sensor electrodes 620, 630. The remaining working electrode extensions 624a-b are similarly situated with opposing side edges adjacent respective portions of the reference electrode 630. That is, the working electrode extension 624b is symmetrically surrounded by the reference electrode extensions 634c and 634b, and the working electrode extension 624a is symmetrically surrounded by the reference electrode extensions 634b and 634a.

In some embodiments, at least one of the dimensions of the working electrode 620, such as its width, can be less than 100 micrometers. In some embodiments, the working electrode 620 is a microelectrode with at least one dimension of about 25 micrometers. In some cases, the working electrode 620 can have a width of about 10 micrometers, or a width (or other dimension) between 10 and 100 micrometers. For example, the width $w_{WE}$ of each of the extensions 624a-c can be about 25 micrometers. The reference electrode 630 can have an exposed area that is about five times larger than the exposed area of the working electrode 620. In some examples, the width $w_{RE}$ of the reference electrode extensions 634a-d can be approximately five times larger than the width $w_{WE}$ of the working electrode extensions 624a-c. Thus, the reference electrode extensions 634a-d may have a width $w_{RE}$ of about 125 micrometers and the working electrode extensions 624a-c may have a width $w_{WE}$ of about 25 micrometers.

The length of the working electrode extensions 624a-c (e.g., distance between the base 622 and the distal end 627) can be selected to provide a desired total cumulative length of all working electrode extensions 624a-c (i.e., the length of the first extension 624a plus the length of the second extension 624b plus the length of the third extension 624c). As noted above, the sensitivity of the electrochemical sensor 601 is determined, at least in part, by the number of induced electrochemical reactions occurring with an analyte upon exposing the analyte to the sensor electrodes 620, 630. Because electrochemical reactions are induced preferentially along the side edges of the working electrode 620 adjacent to respective sections of the working electrode 630, where the local voltage gradient is greatest (e.g., along the side edges 625, 626 of the extension 624c, and the side edges of the other extensions 624a-b), the sensitivity of the electrochemical sensor 601 depends, at least in part, on the total length of such side edges. In some embodiments, desired sensor sensitivity is achieved by configurations having a total cumulative length of working electrode extensions of about 1000 micrometers. In such a symmetric configuration, the total length of working electrode side edges situated adjacent respective portions of the reference electrode is approximately double the total cumulative length (e.g., about 2000 micrometers). Thus, some embodiments may include configurations with a working electrode that has two extensions, each about half of the total desired cumulative length; other embodiments may include configurations with a working electrode that has three extensions (as in FIG. 6A), and each may be about a third of the total desired cumulative length. Other cumulative lengths of the working electrode 620 can also be selected to provide a desired total length of working electrode side edges adjacent respective sections of the reference electrode to achieve a desired sensor sensitivity.

The thickness of the sensor electrodes 620, 630 (e.g., height on the substrate) can be 1 micrometer or less. The thickness dimension can be, for example, between about 1 micrometer and about 50 nanometers, such as approximately 500 nanometers, approximately 250 nanometers, approximately 100 nanometers, approximately 50 nanometers, etc. In some cases the working electrode 620 can be a conductive material patterned on a substrate to have a width of about 25 micrometers, a length of about 1000 micrometers, and a thickness of about 0.5 micrometers. In some embodiments, the reference electrode 622 can be have a similar thickness and can be larger in total area than the working electrode 620. For example, the reference electrode 630 have an area more than five times greater than the area of the working electrode 620.

The electrodes 620, 630 can each be formed by patterning conductive materials on a substrate (e.g., by deposition techniques, lithography techniques, etc.). The conductive materials can be gold, platinum, palladium, titanium, silver, silver-chloride, aluminum, carbon, metals, conductors formed from noble materials, combinations of these, etc. In some embodiments, the working electrode 620 can be formed substantially from platinum (Pt). In some embodiments, the reference electrode 630 can be formed substantially from silver silver-chloride (Ag/AgCl).

Figure 6B:
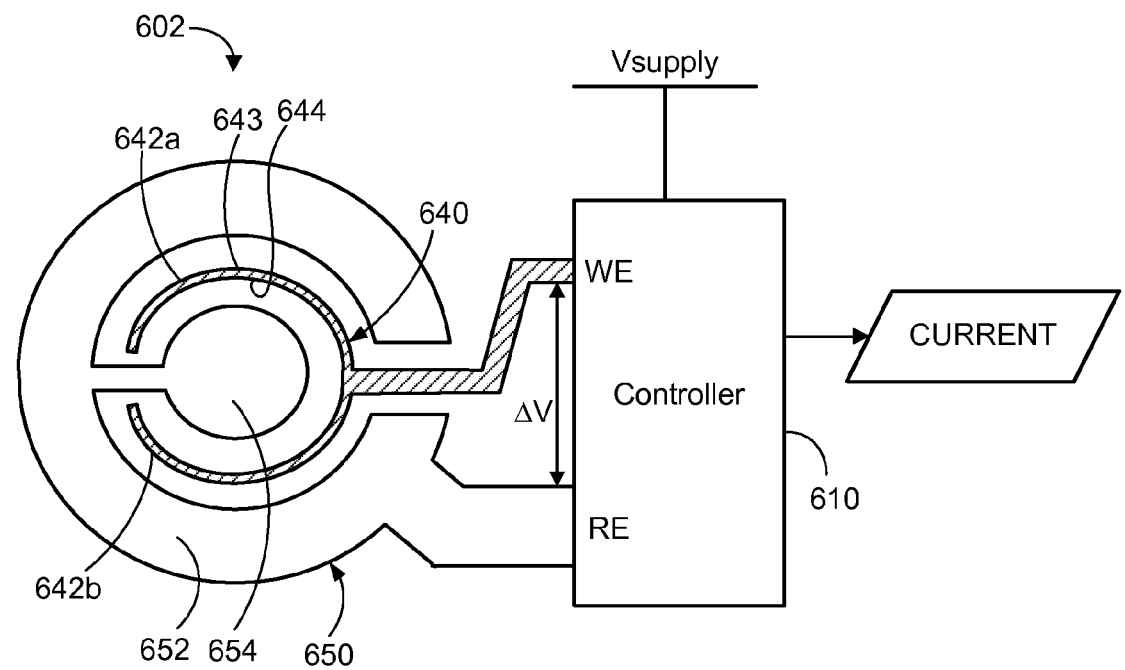
FIG. 6B illustrates another example symmetric arrangement for electrodes in an electrochemical sensor.

FIG. 6B illustrates another example symmetric arrangement for electrodes in an electrochemical sensor 602. The arrangement illustrated by FIG. 6B is not drawn to scale, but instead is provided for explanatory purposes to describe the example arrangement. The electrochemical sensor 602 can be included in an eye-mountable device for detecting tear film oxygen concentrations and/or other analytes (e.g., the eye-mountable devices described in connection with FIGS. 1-3 above). The electrochemical sensor includes a working electrode 640 and a reference electrode 650 arranged as flattened rings situated on a substrate. Similar to the sensor 601 in FIG. 6A, the electrodes 640, 650 are each electrically connected to a controller 610 which operates the sensor 602 by applying a voltage difference $\Delta V$ between the working electrode 640 and the reference electrode 650. The voltage difference $\Delta V$ causes the working electrode 640 to induce electrochemical reactions with an analyte exposed to the sensor electrodes 640, 650, which reactions generate an amperometric current that can be measured through the working electrode 640.

For clarity in the drawings, the working electrode 640 is illustrated with a hatch pattern while the reference electrode 650 is not. The reference electrode 650 can include an outer ring section 652 and an inner ring section 654, with the working electrode 640 interposed between the two sections 652, 654 of the reference electrode 650. The interposed portion of the working electrode 640 is a ring-shaped region with a cutout to allow for an interconnect between the sections 652, 654 of the reference electrode 650. The ring-shaped region of the working electrode 640 includes a first portion 642a and a second portion 642b that are each approximately semicircular arcs joined to a base section that passes through a cutout in the outer ring section 652 of the reference electrode 650. The two portions 642a-b of the working electrode 640 are arranged with opposing side edges each adjacent respective sections 652, 654 of the reference electrode 650. For example, the first portion 642a of the working electrode 640 includes an outer side edge 643 and an inner side edge 644, which can each be shaped as approximately concentric semicircular arcs. The outer side edge 643 is adjacent the outer ring-like section 652, and the inner side edge 644 is adjacent the inner ring-like section 654. Similar to the symmetric arrangement of the sensor 601 described above in connection with FIG. 6A, the working electrode 640 is surrounded on opposing side edges (e.g., the side edges 643, 644) by respective sections 652, 654 of the reference electrode 650. Thus, the sensor 602 induces electrochemical reactions with at least approximately equal efficiency along both sides of the working electrode 640.

The flattened rings can be arranged concentrically (e.g., with a common center point) such that the separation between the electrodes 640, 650 is substantially uniform along the circumferential edges of the electrodes 640, 650. In other examples, the separation between the opposing side edges of the working electrode 640 and the reference electrode 650 can have a tapered (or other varying) gap distance that varies symmetrically along the length of the extensions 624*a-b* such that the separation distance is symmetric between the opposing side edges (e.g., the opposing sides 643, 644).

The extensions 642*a-b* of the working electrode 640 can have a width of about 25 micrometers, a thickness of about 500 nanometers, and a total cumulative length of about 1000 micrometers. The reference electrode 650 can have a total area that is about five times greater than the area of the working electrode 640 (e.g., the radial width of the first and second sections 652, 654 can be approximately 125 micrometers while the width of the working electrode extensions 642*a-b* can be about 25 micrometers). However, the concentric ring arrangement may be implemented with other dimensions.

In some embodiments, the working electrode can be arranged with multiple extensions forming at least portions of roughly concentric rings (i.e., arcs). Each such extension can be surrounded, symmetrically, by respective sections of the reference electrode such that the extensions have similar voltage gradients along opposing side edges, which can then be used to induce electrochemical reactions with similar efficacy.

Figure 7A:
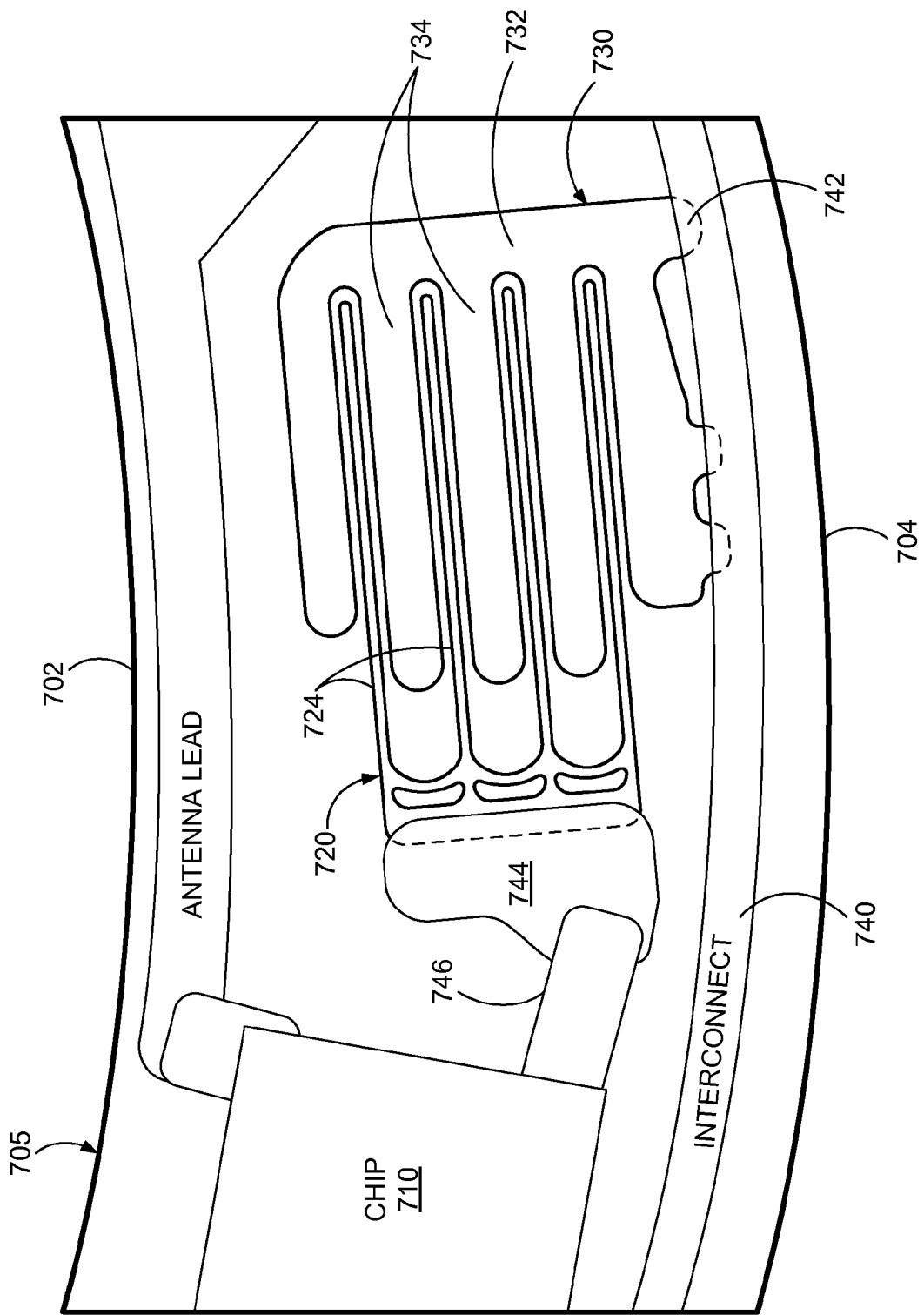
FIG. 7A illustrates an example coplanar arrangement for electrodes in an electrochemical sensor disposed on a surface of a flattened ring substrate.

FIG. 7A illustrates an example coplanar arrangement for electrodes in an electrochemical sensor disposed on a surface of a flattened ring substrate. FIG. 7A illustrates a portion of a substrate 705 on which an electrochemical sensor is mounted. The substrate 705 is configured to be embedded in an eye-mountable device and can be similar to the substrate 230 described above in connection with FIGS. 1-5. The substrate 705 can be shaped as a flattened ring with an inner edge 702 and an outer edge 704. The two edges 702, 704 may both be at least approximately circular, although only a portion of each is shown in FIG. 7A.

The substrate 705 provides a mounting surface for mounting a chip 710 and for patterning sensor electrodes, an antenna, and conductive interconnects between pads or terminals on the chip 710 and the other components. An electrochemical sensor includes a working electrode 720 and a reference electrode 730 patterned in an interdigitated arrangement. The working electrode 720 includes four fingers 724 that can each have a relatively narrow width (e.g., about 25 micrometers). The working electrode 720 is electrically connected to a connection pad of the chip 710 through a pair of overlapped interconnects 744, 746. The reference electrode 730 includes fingers 734 that extend from a base 732. As shown in FIG. 7A, the fingers 724, 734 of the two electrodes 720, 730 can be at least approximately parallel with one another. Moreover, the electrodes 720, 730 can be arranged in an interdigitated arrangement such that each of the fingers 724 of the working electrode 720 is interposed between two of the fingers 734 of the reference electrode in an at least approximately symmetric manner. As such, each of the working electrode fingers 724 has a similar voltage gradient along both opposing side edges. The reference electrode 730 can then be electrically connected to another pad (not visible) on the chip 710 via the interconnect 740 that connects to the reference electrode 730 at multiple overlap points 742.

The chip 710 can also be connected to other components via additional connection pads. For example, as shown in FIG. 7A, the chip 710 can be connected to an antenna lead, which can be formed of a patterned conductive material, such as electroplated gold, for example, that substantially circles the substrate 705 to create a loop antenna.

Figure 7B:
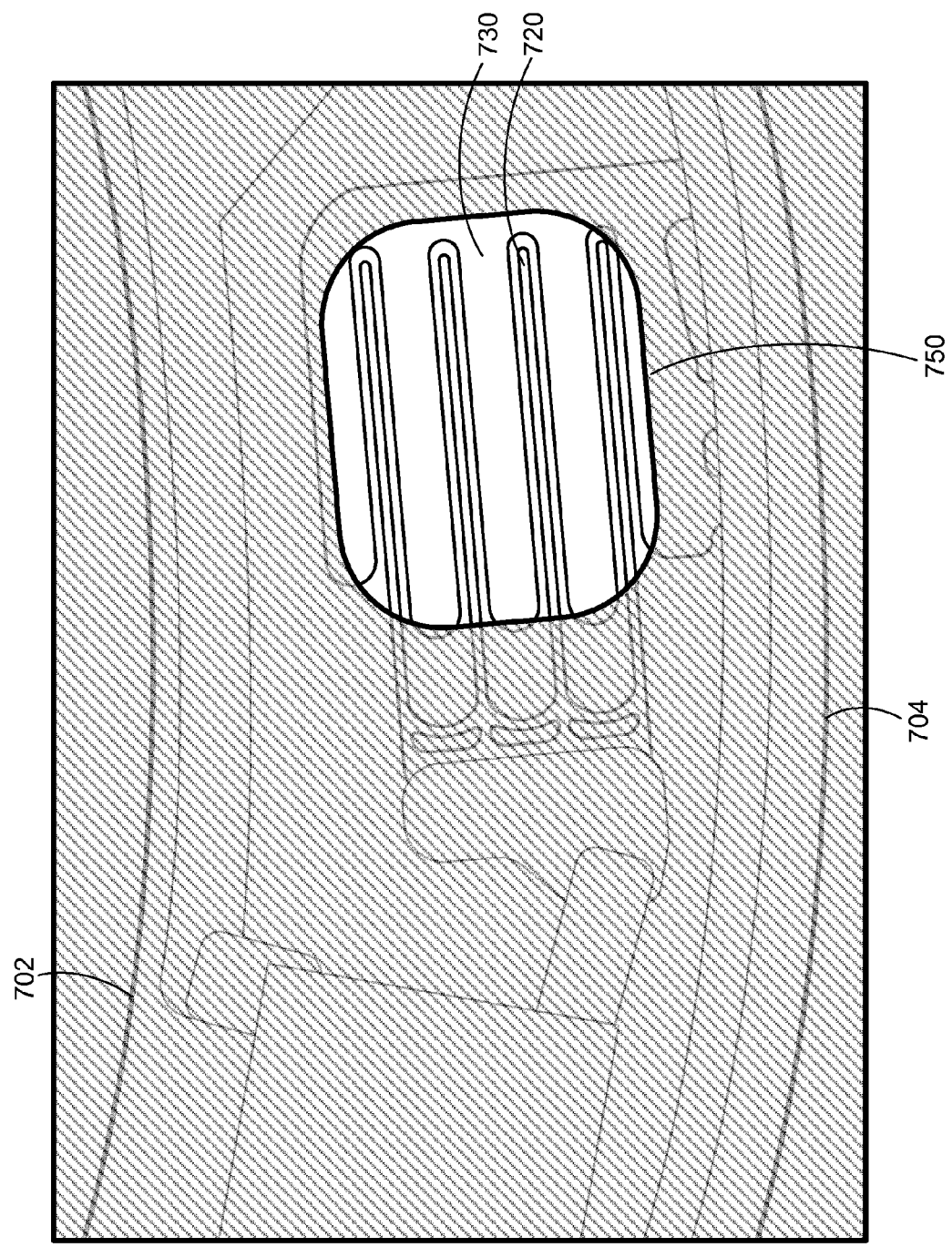
FIG. 7B illustrates the arrangement in FIG. 7A when embedded in a polymeric material with a channel positioned to expose the electrochemical sensor electrodes.

FIG. 7B illustrates the arrangement in FIG. 7A when embedded in a polymeric material with a channel 750 positioned to expose the electrochemical sensor electrodes 720, 730. In FIG. 7B, the polymeric material is illustrated by the hash pattern that is superimposed over the portion of the substrate 705 shown in FIG. 7A. The channel 750 may be formed by removing a portion of the encapsulating polymeric material (e.g., by etching, by removing a layer defined by a photoresist, etc.). The channel 750 exposes a region including the sensor electrodes 720, 730, such that tear film coating the polymeric material is able to directly contact the sensor electrodes 720, 730, and an analyte therein is able to electrochemically react at the electrodes. The exposed region created by the channel 750 can include a desired cumulative length of the working electrode 720 (e.g., a cumulative length of approximately 1000 micrometers).

In the sensor electrode arrangement shown in FIG. 7A-7B in which the electrodes are mounted on the substrate 705, the extended fingers 724, 734 of the two electrodes 720, 730 are each oriented at least approximately tangential to the side edges 702, 704 of the substrate. In other words, the inter-digitated fingers 724, 734 have lengths that are locally parallel to the side edges 702, 704. As such, the electrodes 720, 730 are more able to comply with curvature in the substrate 705. Arranging the electrode fingers 724, 734 to be locally parallel to the side edges causes each of the electrode fingers 724, 734 to be located along a single radius of curvature, even as the substrate 705 conforms to a convex curvature of an eye-mountable device (or adjusts to stresses or strains of being contact-mounted to an eye). For example, if the substrate 705 is curved to comply with the concave curvature of an eye-mountable device in which the substrate 705 is embedded, the individual finger extensions 724, 734 can conform to the local radius of curvature at each location without substantially influencing the inter-electrode spacing. By contrast, an arrangement with finger extensions that cross multiple radiuses of curvatures may be urged to adjust its inter-electrode spacing in a non-uniform manner, along the length of the finger extensions.

While not specifically illustrated in FIG. 7A-7B, the electrochemical sensor may also include a reagent layer that immobilizes a suitable reagent near the working electrode 720 so as to sensitize the electrochemical sensor to a desired analyte.

Moreover, it is particularly noted that while the electrochemical sensor platform is described herein by way of example as an eye-mountable device or an ophthalmic device, it is noted that the disclosed electrochemical sensor and electrode arrangements therefore can be applied in other contexts as well. For example, electrochemical analyte sensors disclosed herein may be included in wearable (e.g., body-mountable) and/or implantable amperometric analyte sensors. In some contexts, an electrochemical analyte sensor is situated to be substantially encapsulated by bio-compatible polymeric material suitable for being in contact with bodily fluids and/or for being implanted. In one example, a mouth-mountable device includes a bio-sensor and is configured to be mounted within an oral environment, such as adjacent a tooth or adhered to an inner mouth surface. In another example, an implantable medical device that includes a bio-sensor may be encapsulated in biocompatible material and implanted within a host organism. Such body-mounted and/or implanted bio-sensors can include circuitry configured to operate an amperometric sensor by applying a voltage across sensor electrodes and measuring a resulting current. The bio-sensor can also include an energy harvesting system and a communication system for wirelessly indicating the sensor results (i.e., measured current). The sensor electrodes can also be substantially co-planar and the working electrode can include relatively narrow extensions that are interdigitated with respect to the portions of the reference electrode. The sensor electrodes can be symmetrically arranged with a working electrode substantially surrounded by portions of a reference electrode such that voltage gradients along opposing side edges of the working electrode are substantially symmetric. The sensor electrodes in such amperometric bio-sensors can be arranged similarly to any of the symmetrically arranged electrodes disclosed above in connection with the example eye-mountable devices described in connection with FIGS. 6A-7B.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. An eye-mountable device comprising:
   a polymeric material having an eye-facing surface and an outward facing surface, wherein the polymeric material is configured to be removably mounted in front of an eye surface;
   a substrate at least partially embedded within the polymeric material;
   an antenna disposed on the substrate;
   an electrochemical sensor disposed on the substrate and including (i) a working electrode having a first side edge and a second side edge, and (ii) a reference electrode situated such that at least a portion of the first and second side edges of the working electrode are adjacent respective sections of the reference electrode; and
   a controller electrically connected to the electrochemical sensor and the antenna, wherein the controller is configured to: (i) apply a voltage between the working electrode and the reference electrode sufficient to generate an amperometric current related to the concentration of an analyte in a fluid to which the eye-mountable device is exposed; (ii) measure the amperometric current; and (iii) use the antenna to indicate the measured amperometric current,
   wherein the substrate is a ring-like structure having inner and outer edges,
   wherein the working electrode and the reference electrode each include a plurality of interdigitated extensions oriented on the substrate to be locally parallel to the inner and outer edges of the ring-like structure at one or more locations along the interdigitated extensions.

2. The eye-mountable device according to claim 1, wherein the working electrode includes a plurality of extensions extending from a base, and wherein each of the plurality of extensions includes a first side edge and a second side edge that are at least partially adjacent to respective sections of the reference electrode.

3. The eye-mountable device according to claim 2, wherein the plurality of extensions of the working electrode and the respective sections of the reference electrode are interdigitated with one another.

4. The eye-mountable device according to claim 1, wherein the respective sections of the reference electrode adjacent the working electrode are arranged symmetrically along the first and second side edges of the working electrode such that while the voltage is applied, a resulting voltage gradient is substantially symmetric along the first and second side edges of the working electrode.

5. The eye-mountable device according to claim 1, wherein the working electrode and the reference electrode are substantially co-planar.

6. The eye-mountable device according to claim 5,
   wherein the working electrode and the reference electrode are arranged as substantially parallel interdigitated extensions, and
   wherein the working electrode includes an extension that is approximately equidistant respective extensions of the reference electrode such that while the voltage is applied, a resulting voltage gradient along opposing side edges of the extension is substantially symmetric between the opposing side edges.

7. The eye-mountable device according to claim 5,
   wherein the working electrode and the reference electrode are arranged as substantially concentric partial rings, and
   wherein the working electrode includes a partial ring that is approximately equidistant respective partial rings of the reference electrode, along a radial direction of the concentric arrangement, such that while the voltage is applied, a resulting voltage gradient along opposing circular side edges of the working electrode partial ring is substantially symmetric between the opposing circular side edges.

8. The eye-mountable device according to claim 1, wherein the inner edge and the outer edge are substantially concentric rings centered about an axis of symmetry of the eye-facing and outward facing surfaces of the polymeric material.

9. The eye-mountable device according to claim 1, wherein the polymeric material includes a channel configured to expose the working electrode and reference electrode to tear film coating the polymeric material.

10. The eye-mountable device according to claim 9, wherein the channel exposes a region occupied by one or more extensions of the working electrode having a combined length of about 1 millimeter.

11. The eye-mountable device according to claim 1, wherein the working electrode has at least one dimension that is about 25 micrometers or less.

12. The eye-mountable device according to claim 11, wherein the at least one dimension of the working electrode is a width between the first side edge and the second side edge.

13. The eye-mountable device according to claim 11, wherein the respective sections of the reference electrode situated adjacent the working electrode have an area that is at least about five times an area of the working electrode.

14. The eye-mountable device according to claim 1, further comprising a reagent that selectively reacts with the analyte, wherein the reagent is localized proximate the working electrode.

15. The eye-mountable device according to claim 1, wherein the polymeric material is a substantially transparent vision correction lens and is shaped to provide a predetermined vision-correcting optical power.

16. A system comprising:
an eye-mountable device including:
   a transparent polymeric material having an eye-facing surface and an outward facing surface, wherein the transparent polymeric material is configured to be removably mounted in front of an eye surface;
   a substrate at least partially embedded within the polymeric material;
   an antenna disposed on the substrate;
   an electrochemical sensor disposed on the substrate and including (i) a working electrode having a first side edge and a second side edge, and (ii) a reference electrode situated such that at least a portion of the first and second side edges of the working electrode are adjacent respective sections of the reference electrode; and
   a controller electrically connected to the electrochemical sensor and the antenna, wherein the controller is configured to: (i) apply a voltage between the working electrode and the reference electrode sufficient to generate an amperometric current related to the concentration of an analyte in a fluid to which the eye-mountable device is exposed; (ii) measure the amperometric current; and (iii) use the antenna to indicate the measured amperometric current; and
a reader including:
   one or more antennas configured to: (i) transmit radio frequency radiation to power the eye-mountable device, and (ii) receive indications of the measured amperometric current via backscatter radiation received at the one or more antennas; and
   a processing system configured to determine a tear film analyte concentration value based on the backscatter radiation,
wherein the substrate is a ring-like structure having inner and outer edges,
wherein the working electrode and the reference electrode each include a plurality of interdigitated extensions oriented on the substrate to be locally parallel to the inner and outer edges of the ring-like structure at one or more locations along the interdigitated extensions.

17. The system according to claim 16, wherein the interdigitated extensions of the working electrode extend from a base.

18. The system according to claim 16, wherein the respective sections of the reference electrode adjacent the working electrode are arranged symmetrically along the first and second side edges of the working electrode such that while the voltage is applied, a resulting voltage gradient is substantially symmetric along the first and second side edges of the working electrode.

19. A device comprising:
   a bio-compatible polymeric material;
   a substrate at least partially embedded within the bio-compatible polymeric material;
   an antenna disposed on the substrate;
   an electrochemical sensor disposed on the substrate and including (i) a working electrode having a first side edge and a second side edge, and (ii) a reference electrode situated such that at least a portion of the first and second side edges of the working electrode are adjacent respective sections of the reference electrode; and
   a controller electrically connected to the electrochemical sensor and the antenna, wherein the controller is configured to: (i) apply a voltage between the working electrode and the reference electrode sufficient to generate an amperometric current related to the concentration of an analyte in a fluid to which the eye-mountable device is exposed; (ii) measure the amperometric current; and (iii) use the antenna to indicate the measured amperometric current,
wherein the substrate is a ring-like structure having inner and outer edges,
wherein the working electrode and the reference electrode each include a plurality of interdigitated extensions oriented on the substrate to be locally parallel to the inner and outer edges of the ring-like structure at one or more locations along the interdigitated extensions.

20. The device according to claim 19, wherein the respective sections of the reference electrode adjacent the working electrode are arranged symmetrically along the first and second side edges of the working electrode such that while the voltage is applied, a resulting voltage gradient is substantially symmetric along the first and second side edges of the working electrode.

* * * * *